US006554819B2

(12) United States Patent
Reich

(10) Patent No.: US 6,554,819 B2
(45) Date of Patent: Apr. 29, 2003

(54) METHOD AND DEVICE FOR PREVENTING CONTRAST ASSOCIATED NEPHROPATHY

(75) Inventor: David Reich, Riverdale, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 126 days.

(21) Appl. No.: 09/757,301

(22) Filed: Jan. 9, 2001

(65) Prior Publication Data

US 2002/0091349 A1 Jul. 11, 2002

(51) Int. Cl.[7] ............................. A61M 37/00; A61M 31/00
(52) U.S. Cl. ........................ 604/508; 604/509; 604/4.01; 604/6.09
(58) Field of Search ............................. 604/4.01, 5.01, 604/96.01, 102.2, 102.3, 508, 6.09, 5.08; 606/194

(56) References Cited

U.S. PATENT DOCUMENTS

| 4,689,041 A | 8/1987 | Corday et al. ................. 604/53 |
| 4,927,412 A | 5/1990 | Menasche ..................... 604/96 |
| 5,069,662 A | 12/1991 | Bodden .......................... 604/4 |
| 5,324,260 A | 6/1994 | O'Neill et al. ................. 604/96 |
| 5,395,331 A | 3/1995 | O'Neill et al. ................. 604/96 |
| 5,423,745 A | 6/1995 | Todd et al. ..................... 604/53 |
| 5,496,277 A | 3/1996 | Termin et al. ............... 604/104 |
| 5,509,900 A | 4/1996 | Kirkman ...................... 604/104 |
| 5,595,181 A * | 1/1997 | Hubbard ...................... 600/481 |
| 5,597,377 A * | 1/1997 | Aldea ........................... 600/16 |
| 5,599,329 A * | 2/1997 | Gabbay ....................... 604/284 |
| 5,759,170 A * | 6/1998 | Peters ..................... 604/164.11 |
| 5,766,151 A * | 6/1998 | Valley et al. ........... 604/103.07 |
| 5,814,016 A * | 9/1998 | Valley et al. ............. 604/96.01 |
| 5,817,046 A | 10/1998 | Glickman ........................ 604/4 |
| 5,833,671 A | 11/1998 | Macoviak et al. ........... 604/247 |
| 5,879,499 A | 3/1999 | Corvi ........................... 156/175 |
| 5,893,841 A | 4/1999 | Glickman .................... 604/101 |
| 5,897,533 A | 4/1999 | Glickman .................... 604/256 |
| 5,919,163 A | 7/1999 | Glickman .................... 604/101 |
| 6,293,920 B1 * | 9/2001 | Sweezer et al. ........... 604/4.01 |
| 6,398,752 B1 * | 6/2002 | Sweezer et al. ............. 128/898 |

FOREIGN PATENT DOCUMENTS

| US | WO98/08455 | 3/1998 |
| US | WO99/11316 | 3/1999 |

* cited by examiner

Primary Examiner—Henry Bennett
Assistant Examiner—Alfred Basichas
(74) Attorney, Agent, or Firm—Darby & Darby

(57) ABSTRACT

A method and device for preventing contrast associated nephropathy are disclosed. When contrast solution is injected into the coronary artery of a patient, blood is prevented from flowing through the coronary sinus into the right atrium. The blood in the coronary sinus is bypassed to a filtration device which filters out the contrast solution from the blood and recirculates the blood back to the patient. Preferably, blood flow from the coronary sinus is blocked by a balloon catheter which includes a port distal of the balloon so that when the sinus is occluded, blood flows from the sinus into the central lumen of the catheter where it can be directed to the filtration device.

8 Claims, 3 Drawing Sheets

METHOD AND DEVICE FOR PREVENTING CONTRAST ASSOCIATED NEPHROPATHY

This invention relates to a method for preventing contrast associated nephropathy and to a catheter designed to be used in the process.

BACKGROUND OF THE INVENTION

Percutaneous transluminal coronary angioplasty (PTCA) has advanced at a rapid pace in terms of efficacy and safety, and is currently the preferred approach in treating coronary atherosclerosis, which produces areas of blockage within a coronary artery.

Prior to performing PTCA and during the procedure itself an iodine containing dye or contrast material is injected into the patient's artery through a catheter. The iodinated solution is fluorescent and enables the coronary arteries to be visualized. The use of the contrast solution, however, includes a certain amount of risk and even though non-ionic compounds, which are inert and hypoallergenic, have been developed, contrast associated nephropathy (damage to the kidneys) is a significant problem. It is common for patients to require revascularization of more than a single vessel but when there is danger of contrast induced renal failure, the vessels must be done on separate visits at greatly increased cost and inconvenience, in addition to the increased risk of arterial puncture. If it were possible to eliminate the risk of renal failure due to the contrast solution, multi-vessel interventions could be done at a single sitting.

In addition, there are many patients with chronic renal insufficiency who, after undergoing catheterization, must wait 24 to 48 hours in the hospital before undergoing PTCA in order to space the kidney load associated with the contrast load. Moreover, the elderly, particularly those with a pre-existing renal insufficiency, comprise a large group in which even angioplasty is not attempted because multi-vessel disease is anticipated and multi-vessel intervention may lead to the risk of renal failure.

Accordingly, despite the significant advances that have been made in treating the coronary arteries themselves (i.e. opening the stenosis with a stent and maintaining it open with anti-platelet drugs), the problems associated with contrast nephropathy have been a limiting factor on the extent to which these advanced angioplasty procedures can be used.

The principal object of the invention is to reduce, if not prevent, the incidence of contrast associated nephropathy during percutaneous coronary procedures.

It is a further object of the invention to provide a catheter which can be used to drain blood from the coronary sinus vein while preventing a substantial amount of the contrast solution from getting into the general circulation of the patient.

SUMMARY OF THE INVENTION

In accordance with the invention, when contrast solution is injected into the coronary artery of a patient, blood is prevented from flowing through the coronary sinus into the right atrium. Simultaneously, the blood in the coronary sinus is bypassed to a device which filters out the contrast solution from the blood and recirculates the blood back to the patient.

In a preferred embodiment, a balloon on a catheter is used to block blood flow from the coronary sinus to the right atrium. The catheter includes a port distal of the balloon so that when the sinus is occluded, blood flows from the sinus into the central lumen of the catheter where it can be directed to the filtration device. Preferably, the balloon is only inflated when the contrast solution is injected and the catheter includes supplemental means for retaining the catheter within the sinus when the balloon is deflated. The supplemental means may include an expandable mechanical device, a second inflatable balloon, or a deflectable tip which can be guided into a branch extending from the sinus.

THE DRAWINGS

DETAILED DESCRIPTION

Contrast nephropathy can be prevented if the contrast solution is kept from the kidney. However, once the dye has been mixed with blood the only way to separate the two is by filtration, typically dialysis. Dialysis relies on diffusion down a concentration gradient and is not effective if the concentration of dye in the blood to be filtered is low. Furthermore, the flow rates of conventional hemodialysis procedures are too high for patients who are undergoing angioplasty and these patients typically do not tolerate wide fluctuations in blood pressure as is common with hemodialysis.

Figure 1:
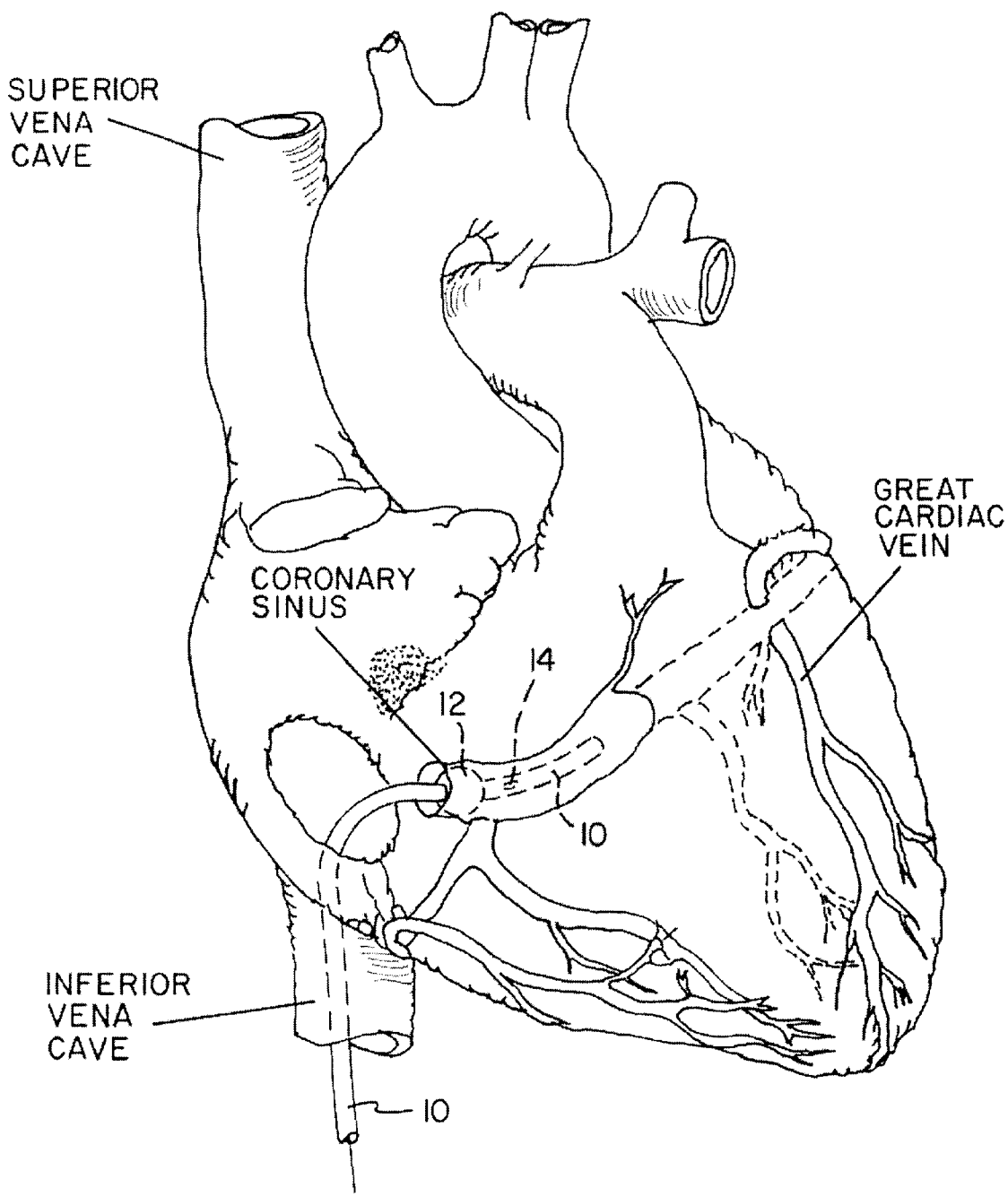
FIG. 1 is an anatomical view of the heart depicting the coronary sinus and its venous branches which empty into the right atrium and showing schematically the position of a catheter in accordance with the invention.

The invention maximizes the filtration of contrast solution from blood by placing a catheter in the coronary sinus where the concentration of dye is the highest. The catheter is provided with means for blocking the flow of blood to the right atrium while at the same time permitting the blood in the coronary sinus to be delivered through the catheter to a filtration machine. The way in which this is accomplished is explained with reference to FIG. 1 which illustrates a heart in which a catheter 10 has been introduced from the groin through the inferior vena cava (IVC) into the coronary sinus (CS). The distal portion of catheter 10 carries a balloon 12 which can be inflated and deflated as required. Balloon catheters are well known and, therefore, the actual catheter construction is not described in detail. In addition to balloon 12, catheter 10 also includes a port 14 distal but close to the balloon which permits blood in the coronary sinus to drain into the catheter lumen when the balloon 12 occludes the coronary sinus.

Figure 2:
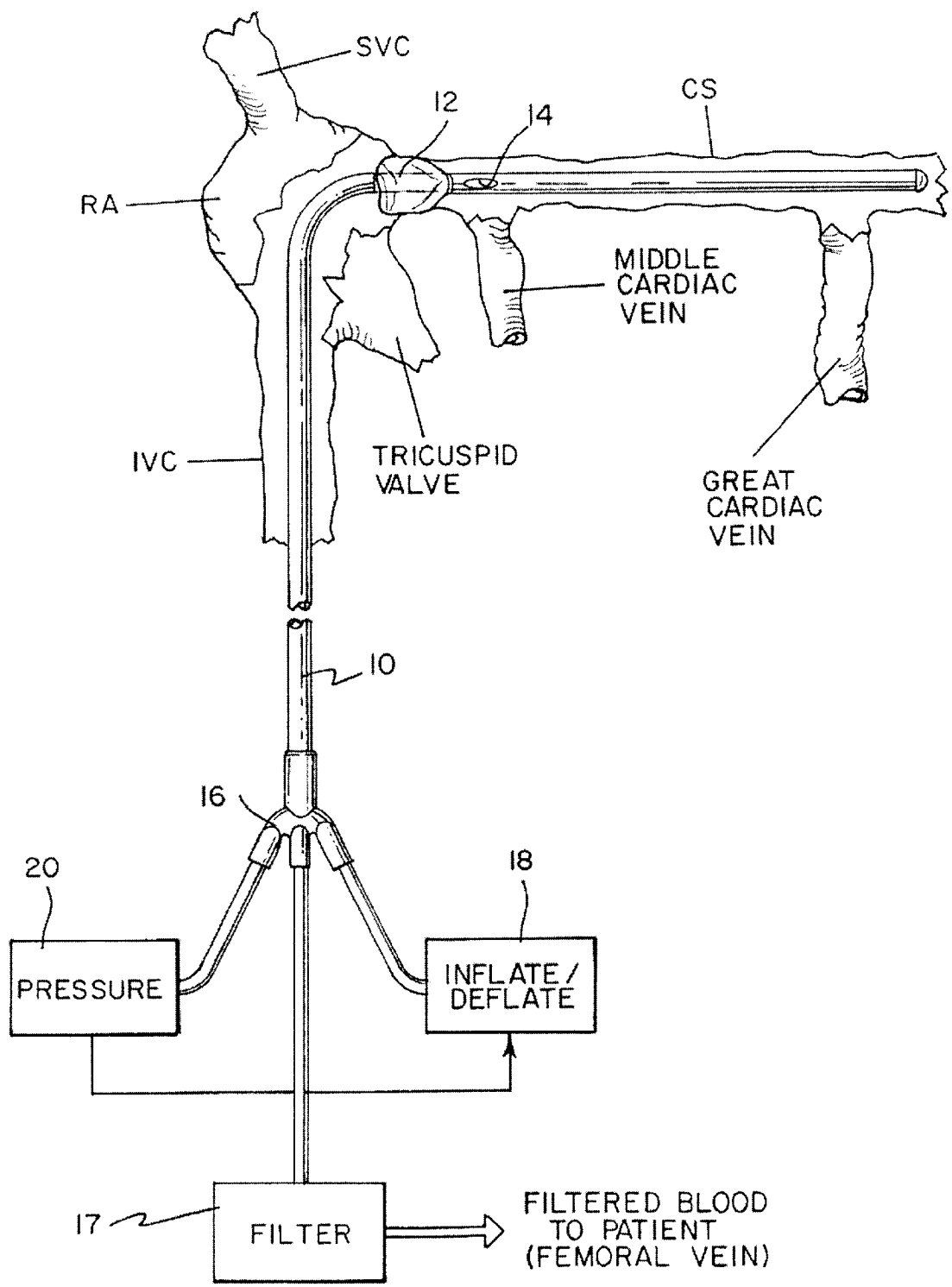
FIG. 2 is a magnified cut away view illustrating schematically how the invention is used to filter contrast solution.

FIG. 2 schematically shows the coronary sinus and right atrium (RA) of a heart. The catheter 10 is positioned preferably with its tapered distal end distal of the coronary sinus and balloon 12 expanded to block blood flow from the coronary sinus to the right atrium. As shown schematically, the proximal end of catheter 10 terminates in a Y-connector 16 (for example) which enables the central lumen of catheter 10 to be connected to a filtration device 17. Catheter 10 will also include an inflation lumen (not shown) which is connected by the connector 16 to a device 18 which can inflate and deflate balloon 12 as described below. Also, as described more fully below, a pressure sensing device may be coupled through a third lumen and connector 16 to a pressure monitoring device 20. In accordance with the invention, when the coronary sinus is blocked by balloon 12, blood flows from the sinus through port 14 and the central lumen of catheter 10 to a blood filtration device 16 which separates the contrast solution and water from the blood. An equal volume of water (or other appropriate crystalloid) is then added to the blood which can be reinfused into the patient in the femoral vein.

The invention contemplates any suitable type of filtration such as dialysis or certrifuging. Continuous veno-venous hemodiafiltration (CVVHD) has been established as a safe and effective way of removing fluid in fluid overloaded critically ill patients and is a suitable dialysis procedure. Moreover, current CVVHD machines are small and relatively simple to use. A "Cell Savers" centrifuge may also be used. Filtration may take place at a flow rate of between about 200 and 400 ml per min (The rate of coronary blood flow is approximately 225–250 ml/min.).

The catheter typically will be passed over a guidewire (not shown) into the coronary sinus. The catheter lumen must be large enough to drain the coronary blood flow and the balloon must be capable of occluding the coronary venous drainage so that none or very little of the contrast rich blood escapes into the right atrium.

It is also contemplated that the catheter will provide a pressure monitoring capability so that if the pressure in the sinus becomes too high or too low, corrective action can be quickly undertaken. For example, if the pressure is too low, the drainage flow rate can be decreased; the flow rate can be increased if pressure is too high. If the pressure remains excessive, it may be necessary to deflate the balloon.

It is possible to leave the balloon inflated throughout the entire procedure; however, this approach has disadvantages. First, although the balloon is inflated at a relatively low pressure (since the coronary venous pressure is low), the risk of trauma to the walls of the sinus may be significant with prolonged inflation and the heart continuously moving. Second, when the balloon is inflated, the filtration catheter is solely responsible for draining all of the coronary blood flow throughout the entire procedure although filtration is only needed for a relatively short period of time after each injection. For example, if the filtration system needs 20 seconds after each injection to clear the contrast from the coronary venous system, and a multivessel angioplasty involves 60 injections of contrast, then the actual filtration of coronary sinus blood takes up only 20 minutes (20×60=1200 seconds or 20 minutes). The procedure, however, may take three hours.

It has been established that intermittent coronary sinus occlusion is a safe procedure during coronary intervention. In the past, the procedure was used to protect the distal myocardium when the artery closed during balloon angioplasty. The purpose was to occlude the sinus and then deflate the balloon in order to allow the venous blood to drain. In accordance with the invention, it is contemplated that the balloon may be inflated only for that period of time required for the injected dye to be intercepted and filtered. For example, if an ACIST™ electronic contrast injection system is employed, the balloon can be inflated automatically for about 15–20 seconds and the filtration apparatus activated for only that same period of time. The balloon would then automatically deflate until the next injection; therefore, the sinus would not be occluded continuously for a long time period. This would minimize the risk of damage to the coronary sinus.

Figure 3:
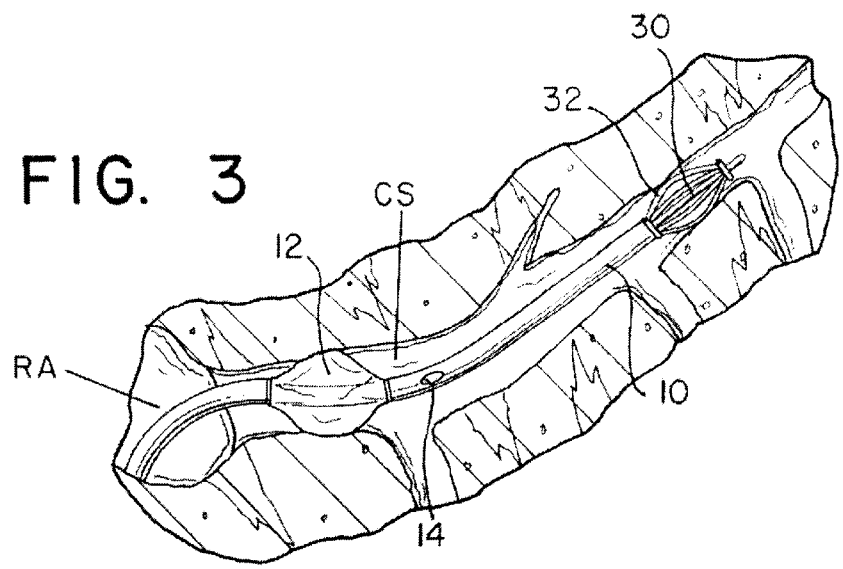
FIGS. 3, 4 and 5 illustrate different embodiments of a catheter for use when occlusion of the sinus is intermittent, showing different means for retaining the catheter within the sinus when the occlusion balloon is deflated.
Figure 4:
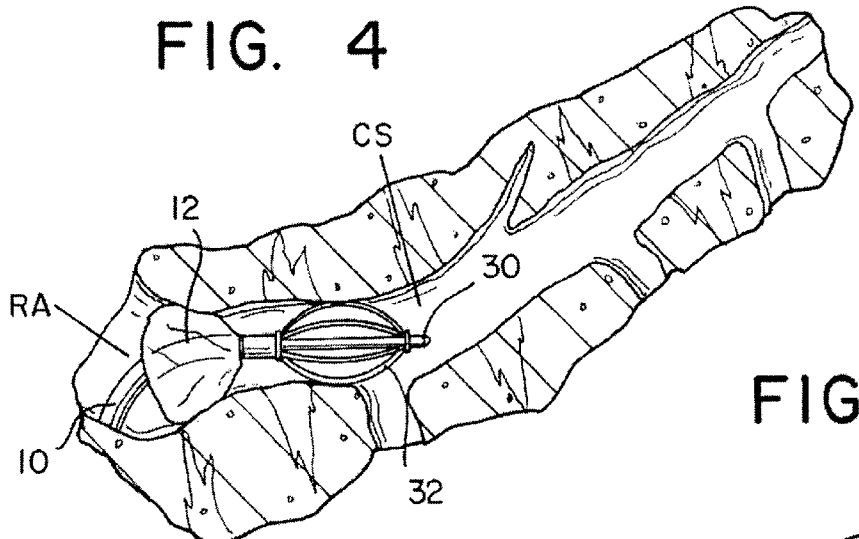
Figure 5:
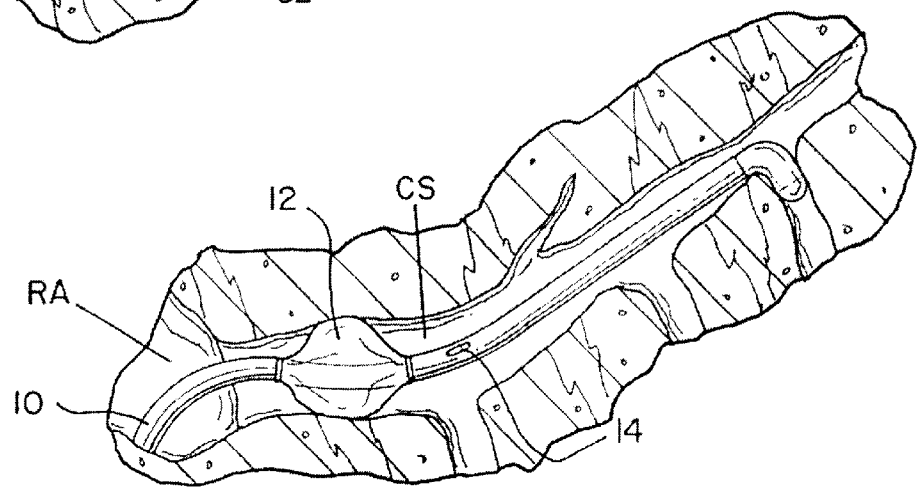

In accordance with this embodiment of the invention, the balloon 12 is inflated only when the contrast is injected. It is maintained inflated while the catheter drains the venous blood (e.g. for 20 seconds) and then automatically deflated, allowing the venous blood to flow around the catheter into the right atrium in the usual fashion. However, if the balloon is only inflated intermittently, there is no mechanism for maintaining the catheter within the sinus when the balloon is deflated and the catheter therefore is subject to displacement by the venous flow. As shown in FIGS. 3–5, a supplemental mechanism on the catheter for stabilizing the catheter may be provided when the balloon used to occlude the sinus is deflated.

Kirkman U.S. Pat. No. 5,509,900 discloses various devices for retaining a catheter in a blood vessel in a fixed position. Any of these devices can be used. FIG. 3 illustrates an expandable basket similar to the configuration shown in FIGS. 38A and 38B of U.S. Pat. No. 5,509,900. In this case, catheter 10 includes a central wire 30 which is axially moveable relative to the catheter. A basket comprises a multiplicity of wires 32 connected at their proximal ends to the catheter 10 and at their distal ends to the movable wire 30. When the wire 30 is extended relative to catheter 10, the wires 32 contract radially. When the wire is retracted, the basket expands as shown in FIG. 3 where it gently engages the walls of the vein so that it can retain the catheter within the sinus when balloon 12 is deflated.

FIG. 4 shows a configuration similar to FIG. 3 wherein a balloon 12 is used to occlude the sinus and an expandable basket 32 used to stabilize the catheter position. In this case, the balloon has a "funnel" shape which is generally complementary to the shape of the sinus so that the balloon extends partially into the right atrium when it is expanded. The basket in this case is positioned close to the balloon. A separate port 14 may not be necessary since blood can flow into the catheter 10 through the space between the catheter and the pull wire 30.

A further embodiment for stabilizing the catheter is shown in FIG. 5. In this design, the distal end of the catheter is directed into one of the branches of the coronary venous system upstream of the sinus (for example, the cardiac vein). Once the distal end of the catheter engages such a branch, it can only be removed by straightening the tip. Catheters are known in which the distal tips are deflectable by the manipulation of pull cables and such a catheter could be directed through the sinus and into the appropriate branch. In general, interventional cardiologists are used to working from the groin and would prefer to perform the contrast filtration from the groin as well. With current catheter constructions, it is difficult to engage the coronary sinus from the groin since the inferior vena cava is not directly aligned with the coronary sinus. With a catheter having a deflectable tip, the catheter would be passed through the inferior vena cava into the right atrium and then deflected so that the tip was near enough to the sinus that a guidewire could be passed deep into the sinus. The catheter would then be released ("undeflected") and passed over the guidewire to the point where the balloon was at the sinus. Once the balloon was properly positioned, the tip would be deflected into the selected branch to stabilize the catheter.

When the procedure is complete, the catheter tip would be simultaneously undeflected and removed. Thus the deflectable tip would accomplish two purposes-engagement of the coronary sinus and stabilization of the catheter during periods when the blood is not being filtered.

It is also contemplated that a specially shaped catheter can be employed so that it can be manipulated by hand into the position illustrated in FIG. 5 without the use of a separate steering mechanism.

The balloon 12 should be relatively large so that it can occlude the sinus at relatively low pressure. This will minimize traumatic injury. The drainage holes should be close to the balloon so as to maximize the amount of contrast rich blood which will be cleansed.

In the preferred embodiment, a balloon is used to occlude blood flow through the sinus. It is contemplated that other types of deployable valve mechanisms could be used as well. For example, an umbrella like mechanism could be expanded when the catheter is properly positioned to block blood flow through the sinus.

The invention can be used to block the flow of contrast solution to the kidneys in other situations where the arteries are imaged by contrast angiography and it is desirable to block the flow of contrast in the vein draining an organ or extremities. For example, contrast angiography is used to image arteries in the legs, dialysis shunts in the arms, and the carotid arteries which lead to the brain. In those cases and others, the invention may be used to prevent contrast associated nephropathy by blocking blood flow from a vein to the patient's kidneys.

What is claimed is:

1. A method for preventing contrast associated nephropathy, comprising inserting a catheter into a patient's coronary sinus, blocking blood flow from the coronary sinus into the right atrium, draining blood from the coronary sinus through the catheter while the blood flow is blocked, and removing contrast solution from the blood which passes through the catheter.

2. A method for preventing contrast associated nephropathy according to claim 1, wherein the blood is returned to the patient after the contrast solution has been removed.

3. A method for preventing contrast associated nephropathy according to claim 1, wherein blood flow is only blocked when the contrast solution is introduced into the patient.

4. A method for preventing contrast associated nephropathy, comprising inserting a balloon catheter into a patient's coronary sinus, expanding the balloon to prevent blood flow from the coronary sinus to the right atrium, draining blood from the coronary sinus through the catheter while blood flow is blocked, filtering the blood from the catheter to remove contrast solution, and returning the filtered blood to the patient.

5. A method for preventing contrast associated nephropathy according to claim 4, wherein the balloon is only inflated when the contrast solution is introduced into the patient.

6. A method for preventing contrast associated nephropathy, comprising inserting a catheter into a patient's vein where there is a high concentration of a contrast solution, blocking blood flow from the vein to the patient's kidney, draining blood from the vein through the catheter while the blood flow is blocked, and removing contrast solution from the blood which passes through the catheter.

7. A method for preventing contrast associated nephropathy according to claim 6, wherein the blood is returned to the patient after the contrast solution has been removed.

8. A method for preventing contrast associated nephropathy according to claim 6, wherein blood flow is only blocked when the contrast solution is introduced into the patient.

* * * * *